United States Patent [19]

Ollmann et al.

[11] Patent Number: 4,898,936

[45] Date of Patent: Feb. 6, 1990

[54] 2-DEOXYURIDINES AND RIBOSIDE PRECURSORS

[75] Inventors: James E. Ollmann; Ralph J. DePasquale, both of Jacksonville, Fla.

[73] Assignee: PCR, Inc., Gainesville, Fla.

[21] Appl. No.: 777,701

[22] Filed: Sep. 19, 1985

Related U.S. Application Data

[63] Continuation-in-part of Ser. No. 653,451, Sep. 24, 1984, abandoned.

[51] Int. Cl.$^4$ .................. C07H 19/073; C07H 11/00; C07H 23/00
[52] U.S. Cl. .................................... 536/17.1; 536/4.1; 536/23
[58] Field of Search ........................ 536/44, 23, 24, 26

[56] References Cited

PUBLICATIONS

Ikehara et al., Advances in Carbohydrate Chemistry and Biochemistry, vol. 36, pp. 135–213, 1979.
Wierenga et al., Carbohydrate Research, vol. 90, pp. 41–52, 1981.

*Primary Examiner*—Ronald W. Griffin
*Assistant Examiner*—L. Eric Crane
*Attorney, Agent, or Firm*—Hedman, Gibson, Costigan & Hoare

[57] ABSTRACT

A process is provided for the preparation of certain 2-deoxyuridines including the steps forming a substituted alkyl 5-O-"protected"-2-deoxyribofuranoside, hydrocarbylating the latter compound, and condensing the hydrocarbylated compound in the presence of a Lewis or Bronsted acid with a silyluracil to form a uridine. Several tritylated ribofuranosides are novel compounds per se.

5 Claims, No Drawings

2-DEOXYURIDINES AND RIBOSIDE PRECURSORS

RELATED APPLICATION

This application is a continuation-in-part of our co-pending application Ser. No.: 653,451 filed 24 Sept. 1984, now abandoned.

This invention relates to a process for producing a therapeutically active material form 2-deoxyribose, and more particularly, to a process for the preparation of 2-deoxyuridines.

BACKGROUND OF THE INVENTION AND PRIOR ART

This invention was made in response to a need for increasing yields of 2-deoxyuridine materials from below about 8% and consequent very high cost. It has now been found that by using a novel sequence of known organic synthesis reactions one is able to produce 2-deoxy uridine materials in substantially higher yield and thus at must lower cost. This process utilizes fewer steps than heretofore used in the production of such derivatives.

Basic organic reactions useful in carrying out the process of the present invention are found in M. Hoffer, Chem. Ber. 93, 2777 (1960), particularly at page 2779, third paragraph et seq.; the book entitled "Protective Groups in Organic Synthesis" by T. W. Green, John Wiley & Sons, Inc., New York, (1981) pp. 10–86; and Ryan et al, J. Org. Chem. 31, page 1181 (1966). Reference may be had to U.S. Pat. Nos. 4,082,911 and 4,209,613 for discussion of the preparation of other nucleosides.

Preferred embodiments of the present invention contain a new step which is both unexpected and surprising in terms of the fact that it proceeds well. All indications were that it would not be likely that a sugar bearing an acid labile protecting group, such as a trityl protected ribofuranoside or a silyl protected ribofuranoside, could be acid condensed with a silylated uracil in an acid catalyzed condensation reaction to form directly a 2-deoxyuridine. Both these protecting groups are regarded as acid sensitive (i.e., easily removed by acid) and the condensation catalyst is a Lewis acid (Friedel-Crafts catalyst) which converts to a Bronsted acid (strong acid) on work up. Not only did the reaction proceed well, but the yields of the end product were much greater than expected. Preparation of a 2-deoxy uridine from trifluorothymidine gave yields in the range of 3% to 8%. By the improved synthesis hereof, yields of the mixed alpha and beta anomers of greater than 50% have been obtained. A beta-2-deoxyuridine produced by our process has been found effective in effecting 50% Sarcoma 180 tumor regression in mice. Also shown herein is a method for converting the alpha-anomer to the beta-anomer, i.e., the alpha-anomer is a precursor to the therapeutically active beta-anomer.

BRIEF STATEMENT OF THE INVENTION

Briefly stated, the present invention is a process for making a 2-deoxyuridine. It comprises the steps of (a) protecting the primary hydroxyl group of an alkyl 2-deoxyribofuranoside with a protecting group selected from triphenyl methyl, substituted triphenyl methyl, and silyl radicals to form a blocked alkyl 5-O-"protected"-2-deoxyribofuranoside; (b) introducing a hydrocarbyl group (e.g., lower alkyl, or arylalkyl) at the 3-O position to form a alkyl 3-O-hydrocarbyl-5-O-"protected"-2-deoxyribofuranoside; (c) condensing a silyluracil with the product of step (b) in the presence of a solvent and a Lewis acid or a Bronsted acid to form a crude 2-deoxyuridine; and optionally (d) deprotecting the protected group in said crude 2-deoxyuridine to form 3'-O-hydrocarbyl-2'-deoxyuridine. The final 2-deoxyuridine is usually obtained as a mixture of alpha and beta anomers. These are preferably isolated from one another for pharmaceutical purposes. Other pharmaceutically acceptable derivatives may be made in a known manner.

After the hydrocarbylation step (b), the trityl group, which is a preferred protecting group for hydrocarbylation, may be replaced with other protecting groups to form a 3-O-hydrocarbyl-5-O-"protected"-2-deoxyribofuranosyl-X wherein X is 1-O-alkyl, 1-O-acyl or 1-halo and the condensation with the silyluracil effected in a manner shown below.

By the term "substituted" as used herein is meant that at least one hydrogen atom in the alkyl or aryl group in question is replaced with a $C_1$–$C_4$ alkyl group, e.g., methyl, ethyl, propyl, isopropyl, n-butyl, isobutyl, t-butyl, etc., a $C_1$–$C_4$ alkoxy group, e.g., methoxy, ethoxy, n-propoxy, isopropoxy, butoxy, isobutoxy, etc., an aryl group, e.g., phenyl, tolyl, etc., a nitro group, a halo group, e.g., chloro, bromo, fluoro, iodo, an acyl group, e.g., acetyl, benzoyl; trifluoromethyl, etc.

DETAILED DESCRIPTION AND SPECIFIC EXAMPLES

The synthesis of these 2-deoxyuridines can begin with ribose although intermediates are commercially available or can be readily synthesized by known procedures. A novel step of this invention responsible for reducing the number of synthesis steps is in the condensation in the presence of an acid of silyluracil with a trityl or silyl protected deoxyribofuranoside. It is surprising that the trityl (triphenyl methyl) group or the silyl group can be used as a protecting group and that such a protecting group remains stable during reaction with the silyluracil under acid condensation conditions. For convenience, the process will be described and illustrated with the production of 3'-O-benzyl-2'-deoxy-5-trifluoromethyluridine.

The scheme for synthesis of the foregoing 2-deoxyuridine may be represented as follows:

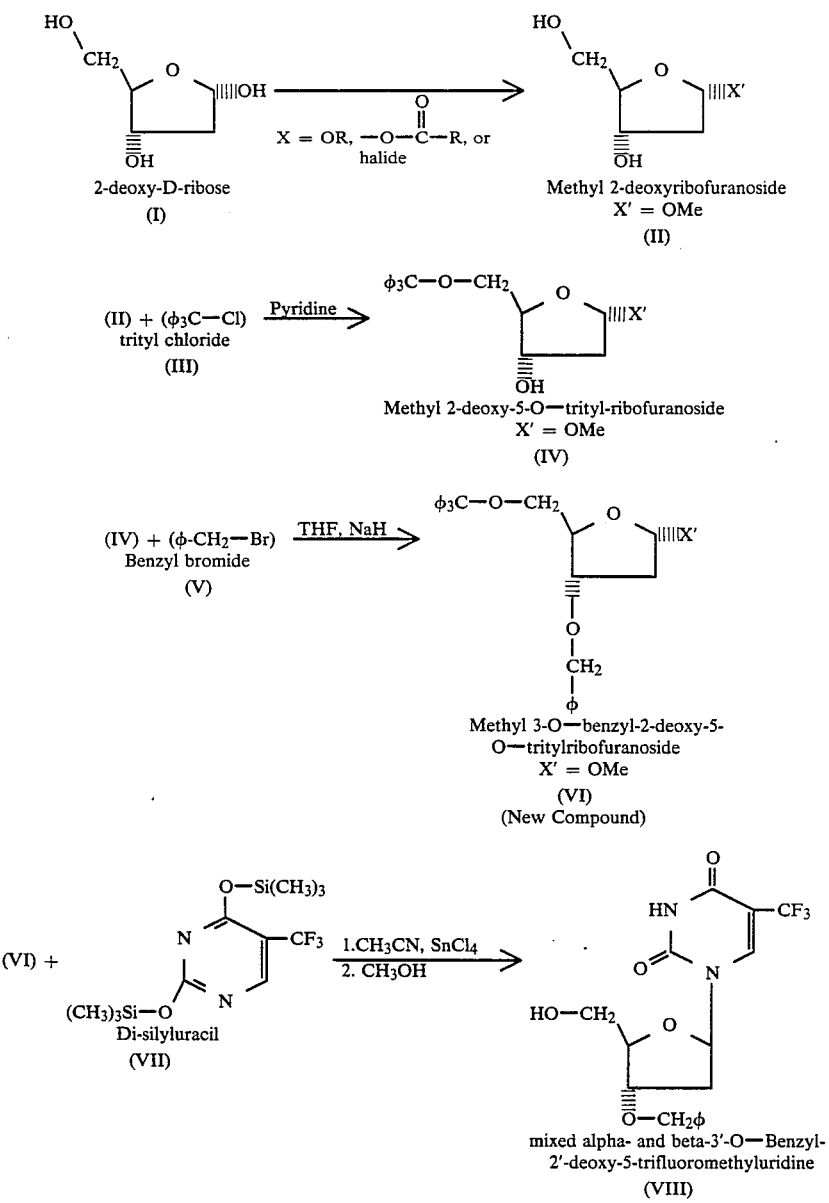

In the foregoing scheme, the secondary OH adjacent the hetrocyclic oxygen in (I) reacts readily with what may be considered a protecting compound such as a lower alkyl alcohol ($C_1$-$C_4$), e.g., methanol, ethanol, propanol, isopropanol, n-butanol, isobutanol, etc., a lower ($C_1$-$C_4$) acyl group, e.g., acetyl, or a halogen, e.g., chlorine. We prefer to form the acetal using an acidified (HCl) lower alkanol, e.g., methanol.

A typical preparation starting with 2-deoxy-D-ribose is as follows:

EXAMPLE I

Methyl 2-Deoxyribofuranoside

To a solution of 10.0 g (0.072 mole) of 2-deoxy-D-ribose in 200 ml anhydrous methanol at 25° C. were added 40.0 ml of 1% HCl/MeOH at approximately 10 ml/min. After the addition was complete, the mixture was allowed to stir under a nitrogen atmosphere for 30 minutes. Pyridine (30 ml) was added (ca. 10 ml/min.) and the mixture was allowed to stir for 10 minutes. The resultant mixture was concentrated on a rotary evaporator followed by the addition of 50 ml of toluene and reconcentration (3 times) affording 10.6 g of a pale yellow oil. Analysis by HPLC (high pressure liquid chromatography) revealed the material to consist of >90% anomers of methyl 2-deoxyribofuranoside with the preponderance of the remainder being anomers of methyl 2-deoxyribopyranoside. The oil was used directly in the next step.

Instead of anhydrous methanol, other lower ($C_1$-$C_4$) alkanols, such as, anhydrous or absolute ethanol, or anhydrous isopropanol may be substituted to form the corresponding acetal. The mode of making such acetals is identical to that illustrated with methanol.

EXAMPLE II

Isopropyl 2-Deoxyribofuranoside

Ten grams of 2-deoxy-D-ribose are dissolved in 180 ml of anhydrous isopropyl alcohol. The solution is allowed to stand overnight at ambient temperature. To this are added 20 ml of a 1% solution of anhydrous HCl in isopropyl alcohol. After stirring for 30 minutes at ambient temperature, the reaction is quenched by the addition of 10 ml of pyridine. The solvent is then removed at reduced pressure affording as a syrup an anomeric mixture of the isopropyl 2-deoxyribofuranoside.

The next step in the process is to protect the primary 5-OH group with a protecting radical, e.g., silyl or, preferably, a trityl radical, by replacing the hydrogen of the primary hydroxyl group as follows:

EXAMPLE III

Methyl 2-deoxy-5-O-tritylribofuranoside

To a solution of 11.2 g (0.07 mole) of methyl 2-deoxyribofuranoside (90% pure) in 60 ml of dry pyridine under a dry nitrogen atmosphere were added 19.0 g (0.07 mole) of triphenylmethyl chloride. The mixture was stirred at ambient temperature for three days. Methanol (35 ml) was then added. The solvents were then evaporated under reduced pressure. The residue was taken up in 200 ml of ethyl acetate, washed with 75 ml of 5% sodium bicarbonate followed by a 75 ml wash with DI (deionized) water. The organic layer was dried ($Na_2SO_4$), filtered and the solvent removed under vacuum affording a sticky, viscous oil. This crude methyl 2-deoxy-5-O-tritylriboruanoside compound was used without further purification in subsequent synthetic procedures.

EXAMPLE IV

Methyl 5-O-(t-Butyldimethylsilyl)-2-Deoxyribofuranoside

To a solution of 22.1 g (0.15 mole) of methyl 2-deoxyribofuranoside (90% pure) in 230 ml dry pyridine under a dry nitrogen atmosphere were added slowly a solution of 21.1 g (0.14 mole) of t-butyldimethylchlorisilane in 70 ml of dry pyridine. The resulting mixture was stirred overnight at ambient temperature. The mixture containing some salts was then heated with stirring at 40°-50° C. for three hours. After cooling to <25° C., dry methanol (25 ml) was added. The mixture was stirred for one hour. The solvents were then removed at reduced pressure affording an oil-salt mixture. This was taken up in a mixture of 200 ml DI water and 200 ml chloroform. The chloroform layer was separated, then washed with an additional 100 ml DI water. The chloroform layer was dried ($Na_2SO_4$), filtered, and the solvent rempoved at reduced pressure. The residual oil was vacuum distilled affording 20.8 g (0.08 mole, 57%) of a colorless oil bp. 91°-98° C. at 0.15 mm Hg, $^1$H NMR ($CDCl_3$) δ0.08 (d, 6, $SiCH_3$), 0.88 (d, 9, t-Bu), 2.05 (m, 2, $CH_2$), 2.8 (broad m, 1, OH), 3.32 (s, 3, —$OCH_3$), 3.38 (s, 2, —$OC^5H_2$), 3.7 (m, 1, —$C^4H$), 4.1 (m, 1, —$C^3\underline{H}$), 5.1 (m, 1, anomeric —CH).

Other inert, preferably aprotic solvents, may be used in the syntheses described herein in place of chloroform, e.g., methylene chloride, carbon tetrachloride, benzene, toluene, acetonitrile, ethylene chloride, ethylene dichloride, dioxane, tetrahydrofuran (THF), dimethylformamide, carbon disulfide, chlorobenzene, sulfolane, molten dimethylsulfoxide, etc.

EXAMPLE V

Methyl 2-Deoxy-5-O-(p-Methoxytrityl)ribofuranoside

To a solution of 30 g (0.182 mole) of methyl 2-deoxyribofuranoside (90% pure) in 250 ml of dry pyridine were added 59.4 grams (0.192 mole) of p-methoxytrityl chloride. The mixture was stirred at ambient temperature under a dry nitrogen atmosphere for 16 hours. Methanol (20 ml) was added and the mixture stirred for an additional 45 minutes. The solvent was removed under vacuum. The residue was taken up in 250 ml of ethyl acetate, washed (4×100 ml) with DI water, and dried ($Na_2SO_4$). The mixture was filtered and the solvent removed under vacuum affording 78.0 grams of the methyl 2-deoxy-5-O-(p-methoxytrityl)ribofuranoside compound as a yellow oil.

The next step is to alkylate or aralkylate the 5-O-protected derivative as follows:

EXAMPLE VI

Methyl 3-O-Benzyl-2-Deoxy-5-O-Tritylribofuranoside

To a stirred mixture of 1.3 g (0.054 mole) of sodium hydride, 10.8 g (7.5 ml, 0.063 mole) of benzyl bromide and 50 ml dry tetrahydrofuran or other aprotic solvent under a dry nitrogen atmosphere were added slowly a solution of 14.8 g (0.038 mole) of crude methyl 2-deoxy-5-O-tritylribofuranoside in 100 ml of dry tetrahydrofuran. After the addition was completed (0.5 hr), the mixture was stirred at ambient temperature for 4 hrs., then at 65°-70° C. for an additional 2 hrs. The mixture was cooled, vacuum filtered through filter-aid, then heated at reflux for 2 hrs. with 15 ml (0.2 mole) of pyridine to consume the excess benzyl bromide. The mixture was again cooled and vacuum filtered through filter-aid. The solvent was removed from the filtrate under reduced pressure. Toluene (2×150 ml) was then added and evaporated. The residue (24.3 g.) was taken up in ethyl acetate (200 ml), washed with saturated NaCl solution (150 ml), then with DI water (150 ml). The organic phase was dried ($Na_2SO_4$), filtered and the solvent evaporated under vacuum. The red-orange oil that remained was used directly in subsequent coupling reactions. An analytical sample was prepared by chromatography on silica gel eluting with 10% ethyl acetate in hexane. The light-yellow oil thus prepared showed the following: $^1$H NMR ($CDCl_3$) δ2.05 (m, 2, $CH_2$), 3.18 (s, 3, $OCH_3$), 3.33 (s, 2, $CH_2$), 3.6 to 4.4 (m, 2, OCH), 4.42 (d, 2, $CH_2$), 4.9 to 5.1 (m, 1, anomeric CH), 7.1 to 7.7 (m, 20, ArH); IR (neat) 3090 cm$^{-1}$(w), 3060 (m), 3035 (m), 2920 (m), 1598 (w), 1490 (m), 1448 (s), 1362 (m), 1080 (s), 762 (m), 748 (m), 705 (s), 633 (m).

The 5-O-trityl group (See formula VI, supra), which may be substituted in one or more of its constituent phenyl groups with $C_1$-$C_4$ alkyl, $C_1$-$C_4$ alkoxy, nitro, halo, etc., groups in, for example, the 4 position, is quite important here if the above product is to be benzylated. The benzylated product itself is novel. After alkylation, it is possible with the addition of a couple of steps to remove the trityl group and replace the trityl group with alkyl, aralkyl, silyl or the like group such as disclosed in the aforesaid book by T. W. Green, supra., and proceed with the synthesis. However, it has been found that the protecting group for the primary OH must be trityl or silyl in order to hydrocarbylate effectively, e.g., benzylate, the secondary OH. The trityl group is preferred to the silyl group because of its better selectivity.

EXAMLE VII

Methyl 3-O-Benzyl-5-O-(t-Butyldimethylsilyl)-2-Deoxyribofuranoside

A mixture of 9.0 g. (0.034 mole) of methyl 5-O-(t-butyldimethylsilyl)-2-deoxyribofuranoside, 15 g (0.19 mole) of benzyl bromide, and 21 g (0.076 mole) silver carbonate in 50 ml dry dimethylformamide or other aprotic solvent is heated at 60° C. under a dry nitrogen atmosphere for five days. The mixture is cooled and the solids filtered. The filtrate is then concentrated at reduced pressure to 30 ml volume. To this are added 20 ml pyridine and the mixture heated at 65° C. for three hours. The solvents are again removed under reduced pressure affording a dark gummy residue which is taken up in a mixture of 150 ml toluene and 100 ml DI water. The organic phase is separated, washed with water (2×100 ml), dried ($Na_2SO_4$) and filtered. The solvent is removed at reduced pressure affording the methyl 3-O-benzyl-5-O-(t-butyldimethylsilyl)-2-deoxyribofuranoside compound as a red oil.

The following Example VII illustrates another hydrocarbylation reaction using a methyl providing agent in lieu of a benzyl providing agent.

EXAMPLE VIII

Methyl 2-Deoxy-3-O-Methyl-5-O-Tritylribofuranoside

To a mixture of 2.6 g (0.11 mole) of sodium hydride in 150 ml of dry tetrahydrofuran under a dry nitrogen atmosphere is added slowly with stirring a solution of 39.0 g (0.10 mole) of methyl 2-deoxy-5-O-tritylribofuranoside in 250 ml of of dry tetrahydrofuran. To this mixture a solution of 17.0 g (0.12 mole) of methyl iodide in 25 ml of tetrahydrofuran is added over a one hour period. The mixture is then stirred at ambient temperature for 20 hours. Methanol (20 ml) is then added slowly to decompose the excess sodium hydride. The solvent and excess methyl iodide are then evaporated under reduced pressure. The residue is then taken up in a mixture of 250 ml of toluene and 150 ml of DI water. The organic phase is separated, washed (2×100 ml) with water, dried ($Na_2SO_4$), filtered, and the solvent removed under reduced pressure affording an anomeric mixture of the methyl 2-deoxy-3-O-methyl-5-O-tritylribofuranoside compound as a yellow oil.

EXAMPLE IX

Methyl 3-O-Benzyl-2-Deoxy-5-O-(p-Methoxytrityl)-Ribofuranoside

A mixture of 5.0 g (13 mmoles) of methyl 2-deoxy-5-O-(p-methoxytrityl)ribofuranoside, 0.5 g (20 mmole) of sodium hydride, and 3.4 g (20 mmole) of benzyl bromide in 50 ml dry tetrahydrofuran was heated at reflux under a dry nitrogen atmosphere for two and one-half hours. The mixture was then stirred at ambient temperature overnight. Pyridine (5 ml) was added and the mixture again heated at reflux for three hours. After being cooled to ambient temperature, the mixture was filtered. The solvent was removed from the filtrate at reduced pressure. The residual oil was taken up in 75 ml ethyl acetate and 50 ml of DI water. The phases were separated and the organic phase washed (2×50 ml) with water. The solution was dried ($Na_2SO_4$), filtered, and the solvent removed under vacuum affording 6.5 g (12.7 mmole, 98%) of the methyl 3-O-benzyl-2-deoxy-5-O-(p-methoxytrityl)ribofuranoside compound as an orange oil.

EXAMPLE X

3'-O-Benzyl-2'-Deoxy-5-Trifluoromethyluridine

To a solution of 11.1 g (0.021 mole, 90% pure) of methyl 3-O-benzyl-2-deoxy-5-O-tritylribofuranoside in 125 ml acetonitrile under a dry nitrogen atmosphere were added 6.8 g (6.2 ml, 0.021 mole) of Bis-(trimethylsilyl)-5-trifluoromethyluracil. The mixture was cooled to 5° C. with an ice-water bath. Acetonitrile (25 ml) was mixed with 8.3 ml of a $CH_2Cl_2$ solution of anhydrous stannic chloride containing 0.66 grams of $SnCl_4$ per ml (5.46 g, 0.021 mole). This solution was added slowly over a period of ca. 15 minutes to the stirred reaction mixture while maintaining a temperature of <5° C. with an ice bath. After the addition was completed, the mixture was stirred at <5° C. for an additional 30 minutes. The reaction was then quenched by adding 25 ml absolute ethanol. The ice-bath was removed and the mixture stirred for 30 minutes while warming to ambient temperature. The reaction mixture was then poured rapidly into a vigorously stirred mixture of 350 ml of 5% sodium bicarbonate solution and 200 ml of ethyl acetate at 0°-5° C.

After stirring for 5 minutes, the emulsion was vacuum filtered through a pad of filter-aid. The filter was washed with 50 ml of ethyl acetate. The combined filtrate and filter washing was phase separated, the organic layer was washed with 250 ml of deionized water, dried ($Na_2SO_4$), filtered, and the solvent removed under vacuum (50 mm Hg at 45° C.) affording 14.7 g of an orange oil.

The oil was dissolved in 1000 ml of hot toluene. Upon cooling, a gelatinous precipitate formed. This was collected by vacuum filtration, washed with 100 ml fresh toluene and air dried affording 2.8 g (0.0073 mole, 34.5%) of an off-white solid identified as alpha-3'-O-benzyl-2'-deoxy-5-trifluoromethyluridine. An analytical sample was prepared by recrystallization from toluene: $^1$H NMR (DMSO-$d_6$) δ2.5 (m, 2, $CH_2$), 3.37 (s, 2, $HOCH_2$—), 3.5 (m, 1, —OH) 4.25 (m, 1, CHOH), 4.52 (s, 2, —$CH_2\emptyset$), 5.0 (m, 1, CHOH), 6.18 (d, 1, anomeric CH), 7.27 (s, 5, ArH), 8.15 (broad s, C=CH); $[\alpha]_D^{20}$ =24.7° (c 1.0, EtOH).

The filtrate from the isolation of the alpha-anomer was evaporated to dryness affording an orange gummy oil. The oil was triturated with hexane (4×100 ml) to remove trityl ethyl ether. The residual gum (5.5 g) was subjected to HPLC on a preparative silica column using 20% ethyl acetate in hexane as eluent. From a short retention time fraction 0.81 g (0.0021 mole, 10.0%) beta-3'-O-benzyl-2'-deoxy-5-trifluoromethyluridine was isolated by evaporation of the solvent: $^1$H NMR (DMSO-$d_6$) α2.32 (m, 2, 2'—$CH_2$), 3.63 (broad s, 2, 5'—$CH_2$), 4.1 (m, 2, 3', 4'—CH), 4.54 (s, 2, —$CH_2\emptyset$), 5.27 (t, 1, —OH), 6.10 (t, 1, anomeric-H), 7.34 (s, 5, ArH), 8.94 (s, 1, CH=C), 11.88 (s, 1, NH); $[\alpha]_D^{20}$ +39.4° (c 1.0, EtOH).

Reworking of the mother liquor affords roughly another 20% yield of a mixture of both the alpha and beta anomers.

The silylated uracil is prepared by reacting uracil with 1.05 to 1.5 equivalents of silylating agent, e.g., trimethylchlorosilane, for each hydroxy, mercapto, or amino group in the uracil compound. The silylating agent is dissolved in hexamethyldisilazane (0.66 equivalent HMDS to 0.33 equivalent silane) and the uracil/silylating system heated for 5-18 hours. The product is isolated by distillation. Other procedures for forming silylated bases, e.g., silylated uracil will be found in U.S. Pat. No. 4,209,613.

Instead of the Friedal-Crafts catalyst $SnCl_4$, other catalysts such as $TiCl_4$, $BF_3$ etherate, trialkylsilyl ester catalyst (U.S. Pat. No. 4,082,911) may be used.

An example of a pyrimidine (uracil) compound which can be condensed with a tritylated sugar to form a 2-deoxy uridine in accordance herewith is prepared as follows:

EXAMPLE XI

Bis-(Trimethylsilyl)-5-Trifluoromethyluracil

Under a dry nitrogen atmosphere, a mixture of 450 g (2.5 mole) of 5-trifluoromethyluracil, 850 g (5.3 mole) of hexamethyldisilazane (HMDS), and 15 g (0.14 mole) of trimethylchlorosilane was heated at 100°-120° C. until the evolution of ammonia ceased (<5 hrs.). The temperature was then raised and a gentle reflux maintained (125°-130° C.) for one hour. The excess HMDS was removed by distillation at water aspirator pressure. The product was then vacuum distilled (bp. 60°-64° C. at 0.3 mm Hg) affording 730 g (2.25 mole, 90.1%) of the title compound as a hydrolytically sensitive, colorless oil.

The foregoing pyrimidine can be used in coupling reactions leading to the production of the desired 2-deoxyuridine.

EXAMPLE XII

3'O-Benzyl-2'-Deoxy-5-Trifluoromethyluridine

To a stirred mixture of 3.5 g (0.01 mole) of methyl 3-O-benzyl-5-O-(t-butyldimethylsilyl)-2-deoxyribofuranoside and 3.4 g (0.01 mole) of Bis-(trimethylsilyl-5-trifluoromethyluracil in 30 ml of methylene chloride at <5° C. was added a solution of 2.9 g (0.011 mole) of stannic chloride in 5 ml of methylene chloride at ca. 0.25 ml/min. The clear yellow solution was stirred for an additional one and one-half hours at 5° C. during which time the color darkened and a fine precipitate formed. Anhydrous ethanol (11 ml) was then added to the mixture. After warming to ambient temperature, the mixture was filtered removing only a small amount of a solid material. The solvent was then removed under vacuum. The dark residual oil was triturated (3×50 ml) with hexane. The residue was taken up in 100 ml of ethyl acetate, washed with 100 ml of cold saturated sodium bicarbonate solution forming an emulsion. This was vacuum filtered and the filtrate layers separated. The organic phase was washed (2×100 ml) with DI water, dried ($Na_2SO_4$), filtered, and the solvent removed under vacuum affording 1.0 g of a thick yellow oil. This material was chromatographed on 75 cc of silica gel eluting with ethyl acetate/hexane (1:1). From early eluting fractions, 150 mg (0.39 mmole, 3.9%) of crude beta-anomer of the title product was obtained with 200 mg (0.52 mmole, 5.2%) of the alpha-anomer being found in later eluting fractions. The products were identified by thin layer chromatography and $^1H$ NMR analysis.

EXAMPLE XIII

3'-O-Benzyl-2'-Deoxy-5-Trifluoromethyluridine

To a solution of 6.4 g (12.5 mmole) of methyl 3-O-benzyl-2-deoxy-5-O-(p-methoxytrityl)ribofuranoside and 4.2 g (13.0 mmole) of Bis-(trimethylsilyl)-5-trifluoromethyluracil in 50 ml of dry acetonitrile at −50° C. was added slowly (over five minutes) a mixture of 3.9 g (15.0 mmole) of stannic chloride, 4 ml methylene chloride, and 6 ml of acetonitrile. The resulting solution was stirred at −5° C. for an additional 20 minutes. Methanol (15 ml) was then added and the mixture slowly (30 minutes) warmed to ambient temperature. The mixture was then poured into a vigorously stirred, cold solution of 5% sodium bicarbonate (250 ml). To this was added 250 ml of ethyl acetate. After being stirred for ten minutes, this mixture was filtered through a pad of filter-aid. The organic phase of the filtrate was separated, washed (2×150 ml) with 10% NaCl solution, dried ($Na_2SO_4$), filtered, and the solvent removed under reduced pressure affording 7.9 g of an orange oil. The oil was triturated with hexane (4×20 ml) and the semisolid residue taken up in 750 ml of hot toluene. After being cooled overnight in a refrigerator, a gelatinous precipitate formed. This was collected by vacuum filtration, washed with 50 ml fresh toluene and air-dried affording 1.59 g (4.1 mmole, 33%) of the alpha-anomer of the title compound as shown by $^1H$ NMR and TLC. The filtrate was stripped of solvent under reduced pressure affording 3.7 g of an orange oil. Trituration of this oil with hexane (3×25 ml) left 2.2 g of residual oil which was chromatographed on 180 g of silica eluting with 40% ethyl acetate in hexane. Fractions containing the beta-anomer of the title compound (by TLC) were combined affording 0.61 g (1.5 mmole 12.6%) of a yellow oil that solidified on standing. Recrystallization from isopropyl alcohol/hexane afforded analytically pure beta-anomer.

EXAMPLE XIV

3'-O-Benzyl-2'-Deoxy-5-Fluorouridine

To a solution of 4.2 g (0.0061 mole, 73% pure) of methyl 3-O-benzyl-2-deoxy-5-O-tritylribofuranoside in 40 ml of acetonitrile under a dry nitrogen atmosphere were added 2.0 g (0.0067 mole) of Bis-(trimethylsilyl)-5-fluorouracil. The mixture was cooled to <5° C. with a ice-water bath. A solution of 1.5 g (0.0067 mole) of trimethylsilyltrifluoromethanesulfonate in 1.5 ml of methylene chloride was prepared. This catalyst solution was added slowly over a period of ca. five minutes to the stirred sugar/pyrimidine reaction mixture while maintaining a temperature of <5° C. The mixture was stirred at 5° C. for an additional 2½ hours. The reaction was then quenched by slow (~5 min) addition of 10 ml anhydrous methanol while keeping the temperature below <10° C. The quenched mixture was warmed to ambient temperature and stirred for an additional three hours. The mixture was poured into a 25 ml stirred solution of aqueous 6% sodium bicarbonate. The resulting mixture was extracted with two 25 ml portions of ethyl acetate. The organic extracts were combined and washed with 25 ml of water. After being dried over anhydrous sodium sulfate, the solvent was evaporated under reduced pressure. The residue was triturated with 35 ml of hexane to remove by-product methyl trityl ether. The residual tacky solid was dissolved in a minimum of acetonitrile. This solution was then subjected to preparative HPLC using a $C_8$ reverse phase packing (SPHERISORB $C_8$) and 40/60 acetonitrile-$H_2O$ as eluent. There was obtained 0.63 g (0.0019 mole, 30.7%) of alpha-3'-O-benzyl-2'-deoxy-5-fluorouridine as the first eluting nucleoside. Also, 0.46 g (0.0014 mole, 21.9%) of the corresponding beta-anomer was obtained from combined later eluting fractions. $^1H$ NMR (DMSO-d$_6$) α2.3 (m, 2, 2'-CH$_2$), 3.6 (m, 2, 5'—CH$_2$), 4.1 (m, 2, 3' & 4'—CH), 4.5 (s, 2, CH$_2$∅), 5.3 (t, 1, OH), 6.1 (m, 1, anomeric-CH), 7.3 (s, 5, ArH), 8.7 (d, 1, CH=C), 11.9 (s, 1, NH).

EXAMPLE XV

This example illustrates a method for converting the alpha-anomer to the beta-anomer.

3'-O-Benzyl-2'-Deoxy-5-Trifluoromethyluridine from alpha-Anomer

Alpha-3'-O-Benzyl-2'-deoxy-5-trifluoromethyluridine (alpha-anomer, 99+% by HPLC), 5.0 g (0.013 mole), was refluxed for 24 hours with 50 ml hexamethyldisilazane and 2 ml trimethylchlorosilane. The excess reactants were removed by rotary evaporation which was followed by the addition and similar concentration of 2×100 ml toluene. The residue was dissolved in 25 ml CH$_2$Cl$_2$. To this were added 5.4 ml ) 3.9 g; 0.0387 moles) triethylamine and 6.4 ml of a 0.48 g/ml trimethylsilyltrifluoromethanesulfonate/CH$_2$Cl$_2$ solution (3.1 g; 0.014 moles). The mixture was stirred for 1.5 hour at room temperature after which 10 ml of 1% HCl/MeOH were added and stirring continued for 30 minutes. The resulting mixture was poured into 50 ml 6% NaHCO$_3$ and extracted with EtOAc, EtOAc extract washed with 50 ml H$_2$O and dried over Na$_2$SO$_4$. The solvent was removed under reduced pressure. The residue was subjected to HPLC using a spherisorb C$_8$ 3 μm column eluting with 50/50 mixture of CH$_3$CN/H$_2$O.

Analysis showed a mixture of 10–20% titled beta anomer compound in 80–90% alpha-anomer.

As indicated above, the group for protecting the primary OH group on the 2-deoxyribofuranoside, is preferably trityl or substituted trityl. It need not be, and another protecting group, e.g., silyl, may be used and then condensation effected with the silyl uracil with CH$_3$CN/SnCl$_4$, for example. Where alkylation or aralkylation of the 3-0 secondary OH group is to be carried out, a trityl or silyl group is necessary, the trityl group being preferred for the reasons stated above. After the alkylation is complete, the trityl or silyl group may be replaced with another protective group such as acyl, alkyl, silyl, etc., prior to the condensation step. This extra step of replacing the trityl or silyl group has not been found to be necessary because of the surprising stability of these protecting groups in the presence of an acid condensation catalyst.

The alkylation of the tritylated compound (Example VI) introduces a

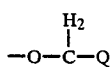

structure. It makes little or no difference what organic radical Q is so long as it survives subsequent reaction conditions. Thus Q may be hydrogen, alkyl (C$_1$-C$_5$) aryl, substituted aryl, heterocyclic, e.g., pyridyl, or containing a heteroatom such as sulfur, nitrogen or phosphorus. A benzyl or methyl group is preferred. These radicals may be substituted with alkoxy, e.g., methoxy, ethoxy, isopropoxy, t-butoxy; nitro; or alkyl, e.g., methyl, ethyl, isopropyl, t-butyl, cyclohexyl, or substituted alkyl, e.g., methoxy methyl, ethoxyethyl, methoxypropyl, chloromethyl, bromomethyl, trifluoromethyl, etc.

To produce the 2-deoxyuridines hereof with deprotected groups, e.g., hydroxyl, the blocking or protecting group or groups can be removed in the usual way, for example, by means of alcoholic solutions of ammonia or alkali metal alcoholates (sodium ethylate) or aqueous or alcoholic alkali.

The beta-anomer can be isolated from the alpha-anomer by high pressure liquid chromatography. The beta-anomer of Example No. XIV is not hygroscopic.

The following studies and preparations have been made by Taiho Pharmaceutical Company Ltd. and are reported in European Patent Publication 0129984 dated Jan. 2, 1985. The 2'-deoxy-5-substituted uridine derivatives of the present invention are useful as antitumor agents. In their use as antitumor agents, they are ordinarily combined with a suitable, pharmaceutically acceptable carrier to be prepared as a pharmaceutical preparation having a form suitable for desired administration purposes. The carrier may be, for example, a diluent, a binder, a lubricant, a coloring agent or a disintegrator, which are conventionally used and pharmaceutically acceptable. The pharmaceutical preparation may take a form of tablet, capsule, granule, powder, liquid or the like for oral administration, as well as a form of injection or the like for non-oral administrations such as intravenous injection. The pharmaceutical preparation may also take a form of suppository for intra-rectal administration. The content of the active ingredient (compound produced by the process of the present invention) per unit form of each pharmaceutical preparation can be appropriately decided so as to be proper for that particular form and is not largely different from those in ordinary pharmaceutical preparations. A preferable content of the active ingredient generally is about 25 to 500 mg per unit. Pharmaceutical preparation of the above forms can be done according to the respective usual methods.

The administration dosage of each pharmaceutical preparation differs naturally from the condition, the weight, the age and the like of a patient to whom the pharmaceutical preparation is to be administered and, accordingly, cannot be restricted. In general, administration to each adult may be made so that the adult intakes about 100 to 2000 mg of the active ingredient daily. This amount of the active ingredient can be administered by division into doses for administration one to six times a day.

Below, there are shown pharmacological tests results, namely, antitumor activity values and toxicity values. Further, based on therapeutic indexes calculated from these two kinds of values, usefulness of the compounds of the present invention will be explained.

Pharmacological tests (a) Method for determining of antitumor activity value $5 \times 10^6$ Cells of mouse-transplantable tumor Sarcoma 180 were transplanted to each male ICR/JCL-strain mouse (having a weight of 27 to 30 g) subcutaneously at the back. Each test compound dissolved or suspended in 0.1% Tween 80 (*)−0.5% CMC (carboxymethylcellulose) solution was orally administered to various test groups each consisting of 7 mice once a day for 7 consecutive days from the next day of tumor transplating, in an amount of 1.0 ml of solution or suspension per 100 g weight per day. As to a control group, the same Tween 80-CMC solution containing no test compound was orally administered once a day for 7 consecutive days in an amount of 1.0 ml per 100 g weight per day.
(*) (A trademark for a series of surface active agents, which are polyoxyethylene derivatives of fatty acid partial ester of sorbitol anhydride, manufactured by I.C.I United States, Inc.)

On the tenth day from the tumor transplanting, an average tumor weight for each administration level of each test compound was determined. This weight was compared with an average tumor weight in control group, and the ratio of tumor enhancement inhibition at each administration level of each test compound compared with control group was calculated. From these calculations, the administration level of each test compound at which the ratio of tumor enhancement inhibition become 50% was obtained and the level (amount) was taken as the antitumor activity value of each compound.

Pharmacological tests-(Continued)

(b) Method for determining toxicity value

Hitherto, toxicity values of anti-malignant tumor agents have been calculated on the bases of $LD_{50}$ of test animals, in most cases. However, $LD_{50}$ is measured under serious conditions of test animal far deviating from conditions of a patient where drugs are actually used and accordingly $LD_{50}$ does not represent a practical toxicity of drug. Therefore, in the present test, accumulated toxicity, which well represents the toxicity of anti-malignant tumor agents, was focused on and, as an indication for sensitive detection of the accumulated toxicity, inhibition of weight increase of the test animal was measured. That is, when antitumor activity value was determined in the above item (a), the weight of each mouse of each test group for each test compound was measured daily from the day of tumor transplating and immediately before administration.

On the day of tumor weight measurement, the average net weight increase of each mouse of each test group for each test compound from the day of tumor transplanting was measured. These increases were compared with the average net weight increase of control group and the ratio of net weight increase of each test group of each test compound to that of control group was calculated. From these calculations, there was obtained an addition amount of each test compound at which weight increase is inhibited by 50% compared with that of control group, and that amount was taken as a toxicity value of each compound.

(c) Calculation of therapeutic index

By the use of the antitumor activity value (hereinafter referred to as A) and the toxicity value (hereinafter referred to as B) of each compound, which were obtained in the above items (a) and (b), respectively, therapeutic index (hereinafer referred to as C) was calculated in accordance with the following equation:

Pharmacological tests-(Continued)

$$\text{Therapeutic index } (C) = \frac{(B)}{(A)}$$

A larger therapeutic index of a compound means that the compound is better balanced in effect and toxicity and more useful.

In Table 1 are shown the results of the above tests, on specific compounds which may be prepared in accordance with the present invention, as well as on comparative compounds, namely, 2'-deoxy-5-trifluoromethyluridine ($F_3TdR$) and 2'-deoxy-5-fluorouridine (FudR).

TABLE 1

| Compound | Antitumor activity value (A) Administration amount of test compound, at which tumor enhancement is inhibited by 50% compared with that of control group (mg/Kg/day) | Toxicity value (B) Administration amount of test compound at which weight increase of test animal is inhibited by 50% compared with that of control group (mg/Kg/day) | Therapeutic Index (C) = (B)/(A) |
|---|---|---|---|
| 3'-O—Benzyl-2'-deoxy-5-trifluoromethyluridine | 17 | 32 | 1.88 |
| 3'-O—Benzyl-2'-deoxy-5-fluorouridine | 17 | 35 | 2.06 |
| $F_3TdR$ | 68 | 49 | 0.72 |
| $F_3TdR$ | 58 | 40 | 0.69 |
| FudR | 93 | 71 | 0.76 |

As is obvious from Table 1, 3'-O-benzyl-2'-deoxy-5-trifluoromethyluridine is equal or superior to $F_3TdR$ and FudR in toxicity and far superior to them in antitumor activity. When compared in therapeutic index, the products of Examples XIII and XIV are especially useful.

Examples of pharmaceutical preparations are illustrated below using the beta anomer of 3'-O-benzyl-2'-deoxy-5-trifluoromethyl uridine.

EXAMPLE OF PHARMACEUTICAL PREPARATION-1 (CAPSULES)

3'-O-Benzyl-2'-deoxy-5-trifluoromethyluridine, lactose, crystalline cellulose and corn starch are mixed in the following proportions. Further, magnesium stearate is mixed with them in the following proportion. This mixture is filled in capsules by the use of a suitable capsule-filling machine so that one capsule contains about 293 mg of the mixture, whereby an intended capsule product is obtained.

| Capsule formulation | mg/capsule |
|---|---|
| 3'-O—Benzyl-2'-deoxy-5-trifluoromethyluridine | 200.0 |
| Lactose | 30.0 |
| Crystalline cellulose | 50.0 |
| Corn starch | 10.0 |
| Magnesium stearate | 3.0 |
| | 293.0 |

EXAMPLE OF PHARMACEUTICAL PREPARATION-2 (GRANULES)

3'-O-Benzyl-2'-deoxy-5-trifluoromethyl uridine, lactose, crystalline cellulose and corn starch are mixed in the following proportion. Thereto is added a 10%-ethanol solution containing hydroxypropyl cellulose and they are kneaded. Then, by the use of an appropriate granulator, the kneaded mixture is made into granules. After drying, the granules are made uniform so as to have granular size of 12 to 42 mesh. Subsequently, the granules are coated with hydroxypropyl methyl cellulose in the following proportion by the use of a suitable coating machine. The coated granules are again made uniform so as to have granular size of 12 to 42 mesh, whereby a granule product is obtained.

| Granule formulation | mg/granule |
| --- | --- |
| 3'-O—Benzyl-2'-deoxy-5-trifluoromethyluridine | 200.0 |
| Lactose | 200.0 |
| Crystalline Cellulose | 311.0 |
| Corn Starch | 200.0 |
| Hydroxypropyl Cellulose | 10.0 |
| Hydroxypropyl Methyl cellulose | 70.0 |
| Fatty Acid Monoglyceride | 3.5 |
| Titanium Dioxide | 5.5 |
| | 1,000.0 |

EXAMPLE OF PHARMACEUTICAL PREPARATION-3 (TABLETS)

3'-O-Benzyl-2'-deoxy-5-trifluoromethyl uridine, corn starch and calcium cellulose glycolate were mixed in the following proportions. A 10%-ethanol solution containing hydroxypropyl cellulose was added, and the mixture kneaded. The kneaded mixture was made into granules by the use of an appropriate granulator. After drying, the granules were mixed with magnesium stearate and silicic acid anhydride in the following proportions and then the mixture made into tablets by the use of a suitable tablet machine. The tablets were coated with hydroxypropyl methyl cellulose, whereby an intended tablet product was obtained.

| Tablet formulation | mg/tablet |
| --- | --- |
| 3'-O—Benzyl-2'-deoxy-5-trifluoromethyl uridine | 200.0 |
| Corn starch | 5.0 |
| Calcium cellulose glycolate | 20.0 |
| Hydroxypropyl cellulose | 2.0 |
| Magnesium stearate | 2.5 |
| Silicic acid anhydride | 2.5 |
| Hydroxypropyl methyl cellulose | 19.999 |
| Polyethylene glycol 6000 | 0.001 |
| Titanium oxide | 2.0 |
| | 254 |

Products such as produced in Examples XIII and XIV show antitumor activity in mice against Sarcoma 180. The effective dose and the lethal dose has been determined as follows:

| | $ED_{50}$ | $LD_{10}$ |
| --- | --- | --- |
| 3'-O—Benzyl-2'-deoxy-5-trifluoromethyluridine | 14 mg/kg. | 80 mg/kg.[+] |
| Trifluorothymidine | 75 mg/kg. | 135 mg/kg. |

Note:
[+]Test animals alive at indicated dose. The dosage is administered orally.

In comparison with the activities of other antitumor agents on Sarcoma 180 in mice, the following results were obtained:

| Compound | $ED_{50}$ (50% tumor regression) |
| --- | --- |
| Trifluorothymidine | 60–80 mg/kg. |
| CF$_3$dC* | 60–80 mg/kg. |
| Ftorafur | 120 mg./kg. |
| 3'-O—Benzyl-2'-deoxy-5-trifluoromethyluridine | 14 mg./kg. |

*5-Trifluoromethyl-2'-deoxycytidine.

What is claimed is:
1. Methyl 3-O-benzyl-2-deoxy-5-O-tritylribofuranoside.
2. Methyl 3-O-benzyl-5-O-(t-butyldimethylsilyl)-2-deoxy-ribofuranoside.
3. Methyl 2-deoxy-3-O-methyl-5-O-tritylbofuranoside.
4. Methyl 3-O-benzyl-2-deoxy-5-O-(p-methoxytrityl)-ribofuranoside.
5. The alpha-3'-O-benzyl-2'-deoxy-5-trifluoromethyluridine.

* * * * *